(12) United States Patent
Scheller et al.

(10) Patent No.: US 8,609,641 B2
(45) Date of Patent: Dec. 17, 2013

(54) (S)-2-N-PROPYLAMINO-5-HYDROXYTETRALIN AS A D3-AGONIST

(75) Inventors: Dieter Scheller, Neuss (DE); Klaus Hansen, Grevenbroich-Münchrath (DE)

(73) Assignee: UCB Pharma GmbH, Monheim (DE)

( * ) Notice: Subject to any disclaimer, the term of this patent is extended or adjusted under 35 U.S.C. 154(b) by 36 days.

(21) Appl. No.: 10/587,637

(22) PCT Filed: Dec. 13, 2004

(86) PCT No.: PCT/EP2004/014143
§ 371 (c)(1),
(2), (4) Date: Feb. 6, 2007

(87) PCT Pub. No.: WO2005/058296
PCT Pub. Date: Jun. 30, 2005

(65) Prior Publication Data
US 2007/0197480 A1    Aug. 23, 2007

(30) Foreign Application Priority Data
Dec. 18, 2003 (DE) .................................. 103 59 528

(51) Int. Cl.
*A61K 31/66* (2006.01)
*A61K 31/27* (2006.01)
*A61K 31/255* (2006.01)
*A61K 31/185* (2006.01)
*A61K 31/135* (2006.01)

(52) U.S. Cl.
USPC ........... 514/114; 514/481; 514/517; 514/553; 514/657

(58) Field of Classification Search
None
See application file for complete search history.

(56) References Cited

U.S. PATENT DOCUMENTS

| | | | |
|---|---|---|---|
| 4,410,519 A | 10/1983 | Seiler et al. ................ | 424/226 |
| 4,465,692 A | 8/1984 | Horn ............................ | 424/330 |
| 5,177,112 A | 1/1993 | Horn ............................ | 514/65 |
| 5,382,596 A | 1/1995 | Sleevi et al. ................. | 514/459 |
| 5,442,117 A | 8/1995 | Stahly et al. ................. | 564/304 |
| 6,372,920 B1 | 4/2002 | Minaskanian et al. ....... | 549/75 |
| 6,884,434 B1 | 4/2005 | Muller et al. ................. | 424/487 |
| 7,067,149 B1 | 6/2006 | Chauveau et al. ........... | 424/465 |
| 7,309,497 B2 | 12/2007 | Rimpler et al. ............... | 424/422 |
| 7,413,747 B2 | 8/2008 | Mueller et al. ............... | 424/448 |
| 7,695,735 B2 | 4/2010 | Chauveau et al. ........... | 424/469 |
| 2003/0026830 A1 | 2/2003 | Lauterback et al. ......... | 424/449 |
| 2003/0027793 A1 | 2/2003 | Lauterback et al. ......... | 514/63 |
| 2003/0166709 A1 | 9/2003 | Rimpler et al. ............... | 514/447 |
| 2004/0034083 A1 | 2/2004 | Stephenson et al. ......... | 514/406 |
| 2004/0048779 A1 | 3/2004 | Schollmayer ................ | 514/2 |
| 2004/0081683 A1 | 4/2004 | Schacht et al. ............... | 424/449 |
| 2004/0116537 A1 | 6/2004 | Li et al. ........................ | 514/663 |
| 2004/0137045 A1 | 7/2004 | Breitenbach et al. ........ | 424/449 |
| 2004/0209861 A1 | 10/2004 | Benavides et al. .......... | 514/210.01 |
| 2005/0033065 A1 | 2/2005 | Mueller et al. ............... | 549/74 |
| 2005/0079206 A1 | 4/2005 | Schacht et al. ............... | 424/449 |
| 2005/0175678 A1 | 8/2005 | Breitenbach ................. | 424/448 |
| 2005/0197385 A1 | 9/2005 | Scheller et al. .............. | 514/438 |
| 2005/0260254 A1 | 11/2005 | Breitenbach et al. ........ | 424/449 |
| 2006/0263419 A1 | 11/2006 | Wolff ............................ | 424/448 |
| 2007/0072917 A1 | 3/2007 | Scheller et al. .............. | 514/357 |
| 2007/0093546 A1 | 4/2007 | Scheller et al. .............. | 514/447 |
| 2007/0191308 A1 | 8/2007 | Kramer ......................... | 514/60 |
| 2007/0191470 A1 | 8/2007 | Scheller ....................... | 514/438 |
| 2007/0197480 A1 | 8/2007 | Scheller et al. .............. | 514/114 |
| 2008/0008748 A1 | 1/2008 | Beyreuther et al. .......... | 424/449 |
| 2008/0138389 A1 | 6/2008 | Muller et al. ................. | 424/448 |
| 2008/0146622 A1 | 6/2008 | Scheller ....................... | 514/357 |
| 2008/0274061 A1 | 11/2008 | Schollmayer et al. ....... | 424/45 |
| 2009/0143460 A1 | 6/2009 | Wolff et al. .................. | 514/438 |
| 2010/0311806 A1 | 12/2010 | Wolff et al. .................. | 514/438 |
| 2011/0104281 A1 | 5/2011 | Beyreuther et al. .......... | 424/486 |
| 2011/0165247 A1 | 7/2011 | Breitenbach ................. | 424/486 |
| 2012/0101146 A1 | 4/2012 | Bouwstra et al. ............ | 514/438 |
| 2012/0215185 A1 | 8/2012 | Schacht et al. ............... | 604/290 |
| 2012/0322845 A1 | 12/2012 | Wolff et al. .................. | 514/438 |

FOREIGN PATENT DOCUMENTS

| | | | |
|---|---|---|---|
| CA | 2092074 | 5/1998 | ............. A61K 9/20 |
| CA | 2483120 | 5/2003 | ........... A61K 31/381 |
| CA | 2787384 | 11/2003 | ........... A61K 31/381 |
| EP | 0 026 848 | 9/1980 | |
| WO | WO 93/01805 | 2/1993 | |
| WO | WO 93/23035 | 11/1993 | |
| WO | WO 94/26703 | 11/1994 | |
| WO | WO 95/04532 | 2/1995 | |
| WO | WO 98/56778 | 12/1998 | |

(Continued)

OTHER PUBLICATIONS

L. Alexander van Vliet, Pieter G. Tepper, Durk Dijkstra, Geert Damsma, Håkan Wikström, et al. Wise Affinity for Dopamine D2, D3, and D4 Receptors of 2-Aminotetralins. Relevance of D2 Agonist Binding for Determination of Receptor Subtype Selectivity J Med Chem 39(21):4233-4237, 1996.*

Daas et al (Nauyn-Schmiedeberg's Arch Pharmacol 342:655-659, 1990).*

Hacksell et al (J Med Chem 22(12):1469-1475, 1979).*

Wikstrom et al (J Med Chem 28:215-225, 1985).*

Rodenhuis (New, centrally acting dopaminergic agents with an improved oral bioavailability: synthesis and pharmacological evaluation, 2000).*

Jansen et al (Naunyn-Schmiedeberg's Arch Pharmacol 343-134-142, 1991).*

(Continued)

*Primary Examiner* — Craig Ricci
(74) *Attorney, Agent, or Firm* — Harness, Dickey & Pierce, P.L.C.

(57) ABSTRACT

The invention relates to a medicament containing (S)-2-N-propylamino-5-hydroxytetralin, the salts or prodrugs thereof. As a D3 agonist, (S)-2-N-propylamino-5-hydroxytetralin is suitable particularly for the treatment of dopa-sensitive movement disorders.

6 Claims, No Drawings

(56) References Cited

FOREIGN PATENT DOCUMENTS

| WO | WO 99/49852 | 10/1999 |
| --- | --- | --- |
| WO | WO 00/27357 | 5/2000 |
| WO | WO 01/38321 | 5/2001 |
| WO | WO 02/15903 | 2/2002 |
| WO | WO 02/089777 | 11/2002 |
| WO | WO 02/089778 | 11/2002 |
| WO | WO 03/028725 | 4/2003 |
| WO | WO 03/029233 | 4/2003 |
| WO | WO 03/092677 | 11/2003 |
| WO | WO 2004/012721 | 2/2004 |

OTHER PUBLICATIONS

Beane (Advance Lubrication Techniques—available online at http://contrails.iit.edu) accessed online May 5, 2011.*
International Preliminary Report on Patentability with full English translation dated Nov. 18, 2005 issued in PCT Application No. PCT/EP2004/014143.
Office Action dated Nov. 1, 2002 issued in U.S. Appl. No. 09/647,290.
Office Action dated Sep. 13, 2007 issued in U.S. Appl. No. 10/936,620.
Office Action dated May 1, 2008 issued in U.S. Appl. No. 10/936,620.
Office Action dated Jan. 26, 2009 issued in U.S. Appl. No. 10/936,620.
Office Action dated Oct. 23, 2009 issued in U.S. Appl. No. 10/565,699.
Office Action dated Nov. 6, 2009 issued in U.S. Appl. No. 10/936,620.
Office Action dated May 27, 2010 issued in U.S. Appl. No. 10/565,699.
Office Action dated Oct. 8, 2010 issued in U.S. Appl. No. 10/936,620.
Office Action dated Feb. 14, 2011 issued in U.S. Appl. No. 10/565,699.
Office Action dated Sep. 19, 2011 issued in U.S. Appl. No. 12/324,166.
Office Action dated Nov. 8, 2011 issued in U.S. Appl. No. 10/565,699.
Office Action dated Apr. 24, 2013 issued in U.S. Appl. No. 10/565,699.
Beaulieu et al. (1984) *Eur. J. Pharmacol.* 105, 15.
Hackling & Stark (2002) *ChemBioChem* 947.
Hacksell et al. (1979) *J. Med. Chem.* 22(12), 1469-1475.
Joyce (2001) *Pharmacol. Ther.* 90; 231-259.
Metman (2001) *Clinical Neuropharmacol.* 24, 163.
Pulvirenti et al. (2002) *Trends Pharmacol. Sci.* 23; 151-153.
Seiler et al. (1986) *J. Med. Chem.* 29; 912.
Sokoloff (1990) *Nature* 347; 146.
Sonesson et al. (1993) J. Medicinal Chemistry 36(22), 3409-3416.
Sonesson et al. (1995) *J. Med. Chem.* 38(8), 1319-29.
Swart et aL (1993) *Toxicology Methods* 3; 279, 289 last paragraph.
Swart et aL (1994) *J. Analytical Toxicology* 18, 71.
Timmerman et al. (1989) Eur. J. of Pharmacology 162(1), 143-150.
Van Vliet et al. (1996) *J. Med. Chem.* 39, 4233.
Wikstroem et al. (1985) J. Medicinal Chemistry 28(2), 215-225.

* cited by examiner

(S)-2-N-PROPYLAMINO-5-HYDROXYTETRALIN AS A D3-AGONIST

This application is a U.S. national stage filing under 35 U.S.C. §371 of International Application No. PCT/EP2004/014143 filed on Dec. 13, 2004, which claims priority of German Application No. DE 103 59 528.7 filed on Dec. 18, 2003. The disclosure of each of the applications identified in this paragraph is incorporated herein by reference in its entirety.

Dopamine is an essential neurotransmitter of the central nervous system. The activity of dopamine is mediated via the binding to five different dopamine receptors. These receptors can be arranged by their morphology and their manner of signal transduction into classes "D1-like" (D1 and D5) as well as "D2-like" (D2, D3 and D4 receptors).

The D3 receptor was first cloned by Sokoloff (Nature 347, 1990, 146) and is especially expressed in the limbic system, in which emotional and cognitive processes are controlled. It is also somewhat less pronounced in the striatal motor tissue where it serves the purpose of fine regulation of movement processes (Joyce, Pharmacol. Ther 90, 2001, 231-259). Recently the D3 receptor has been considered as a promising target for the development of active agents for the treatment of different psychiatric and motor diseases.

Consequently, D3 agonists could represent valuable therapeutics for the treatment of different types of depression, anxiety disorders, sexual dysfunctions, glaucoma, cognitive disorders, restless leg syndrome, attention deficit hyperactivity syndrome (ADHS), hyperprolactinemia, hyperprolactinoma, eating disorders, Parkinson-associated movement disorders, dopa- and neuroleptic-induced movement disorders, e.g., akathisia, rigor, dystonia and dyskinesia, as well as cocaine, alcohol, opiate and nicotine addiction, galactorrhea and acromegaly.

Further, D3 agonists have neuroprotective potential for the treatment and prophylaxis of neurodegenerative disorders (Pulvirenti et al., Trends Pharmacol. Sci. 23, 2002, 151-153; Joyce, Pharmacol. Ther. 90, 2001, 231-259; EP 0 988 296; WO 03/29233; WO 93/23035).

Thus, there is a need for high affinity D3 agonists with preferably greater functional selectivity as compared to "D1-like" receptors and with significant selectivity as compared to the remaining "D2-like" receptors.

It was surprisingly found that (S)-2-N-propylamino-5-hydroxytetralin has the desired characteristics.

Racemic 2-N-propylamino-5-hydroxytetralin is known from the literature.

Hacksell et al (J. Med. Chem. 22, 1979, 1469) evaluated different N-alkylated 2-aminotetralins in regard to their dopamine receptor stimulating activity. A particular dopaminergic activity was demonstrated for the racemic 2-N-propylamino-5-hydroxytetralin. However, the agonistic activity of the substance with an $ED_{50}$ of 40 nM/kg is only moderate and the AUC and the half life are short in comparison to the other evaluated compounds. It was found that aminotetralins with N,N-dialkylation were the most active and appropriate compounds for the intended oral administration.

Beaulieu et al. (Eur. J. Pharmacol. 105, 1984, 15) evaluated N,N-disubstituted 2-aminotetralin in regard to its D2 stimulating activity. The racemic 2-N-propylamino-5-hydroxytetralin demonstrated a moderate activity while N,N-dialkylated 2-amino-5-hydroxy derivate, like N-0437 (racemic rotigotine), showed a significantly higher activity. Conclusions to possible therapeutic potential of 2-N-propylamino-5-hydroxytetralin were not made.

Seiler et al. (J. Med. Chem. 29, 1986, 912) disclose 2-N-propylamino-5-hydroxytetralin as an educt for syntheses of N-dialkylated compounds. A biological activity of 2-N-propylamino-5-hydroxytetralin is not described.

Swart et al. (Toxicology Methods 3, 1993, 279) describe the racemate of 2-N-propylamino-5-hydroxytetralin as rotigotine metabolite with weaker dopaminergic activity. Rotigotine (5,6,7,8-tetrahydro-6-[propyl[2-(2-thienyl)ethyl]amino-1-naphthalenol) is an example of a dopamine receptor agonist with D2/D3 agonistic activity. In comparison to rotigotine, which binds with a $K_d$ value of 5 nM to a dopamine receptor rich membrane fraction, 2-N-propylamino-5-hydroxytetralin demonstrates a clearly higher $K_d$ value of 1.3 µM. The authors come to the conclusion that the N-dealkylated metabolites of rotigotine have a dopaminergic activity too weak for them to have a therapeutic relevance.

Swart et al. (J. Analytical Toxicology 18, 1994, 71) disclose the (S)-enantiomer of 2-N-propylamino-5-hydroxytetralin as a metabolite of rotigotine. A biological activity is not described.

Sonesson et al. (J. Med. Chem. 38, 1995, 1319) evaluated the biological activity of monopropyl analogue of {[(trifluoromethyl)sulfonyl]oxy}-2-aminotetralins. The enantiomers of 2-N-propylamino-5-hydroxytetralin were disclosed as intermediate synthesis products, however they were not biologically characterized.

EP 0 026 848, EP 0 717 620, WO 94/26703 and WO 01/38321 disclose 2-N-propylamino-5-hydroxytetralin as an educt for the synthesis of N-dialkylated and sulfonated aminotetralin. The medical application of 2-N-propylamino-5-hydroxytetralin is not suggested.

Van Vliet et al. (J. Med. Chem. 39, 1996, 4233) evaluate the applicability of competition tests with D2L agonists and D2L antagonists for the prediction of dopamine receptor subtype selectivity. Here aminotetralin is evaluated in regard to its D3 selectivity and potential suitability as antipsychotic. Within the scope of this evaluation, racemic 2-N-propylamino-5-hydroxytetralin was applied as well as 27 other substances. Functional data for (ant)agonistic activity of the used substances was not collected. The medical use of 2-N-propylamino-5-hydroxytetralin is not suggested. On the other hand, the authors come to the conclusion on p. 4236 that, with the exception of compound (+)25, none of the applied substances demonstrate the desired pharmacological profile of a D3 selective antipsychotic.

In summary, the racemic 2-N-propylamino-5-hydroxytetralin is, from the state of the art, known as an unselective, moderately active dopamine agonist with a modest half life. Even though a known dopaminergic activity of the racemic 2-N-propylamino-5-hydroxytetralin has been known since 1969 (see Hacksell et al., supra), a medical use of this substance is not described and is also not suggested. On the contrary, Swart et al. come to the conclusion that the N-dealkylated metabolites of rotigotine have a dopaminergic activity which is too weak to be therapeutically relevant (Tox. Meth. 3, 1993, p. 289, last paragraph).

Consequently, there was no motivation for the skilled person to consider an enantiomeric separation of this obviously therapeutically unsuitable substance and to test the individual enantiomers for their therapeutic potential.

It was therefore surprising that the pure (S)-enantiomer of 2-N-propylamino-5-hydroxytetralin demonstrated a particular affinity to and a noticeable functional selectivity for the D3 receptor as well as a pure agonistic activity, which made the substance a valuable candidate for the treatment of diseases caused by dopamine deficiency. This therapeutically attractive profile of the pure (S)-enantiomer was not identified in the previous studies with 2-N-propylamino-5-hydroxytetralin.

As a matter of fact, the (S)-enantiomer of 2-N-propylamino-5-hydroxytetralin in fact binds with a Ki value of 7.6 nM to the D3 receptor. In comparison, the binding compared to other dopamine receptor subtypes is considerably less pronounced. Overall the receptor binding tests demonstrate a selectivity D3/D1 and D3/D5 of >1000 and of D3/D2 of approx. 40 (Table 1).

TABLE 1

$IC_{50}$ value of (S)-2-N-propylamino-5-hydroxytetralin to receptor subtypes

| Receptor | Ki (nM) |
| --- | --- |
| dopamine D1 (h) | >10000 |
| dopamine D2S (h) | 290 |
| dopamine D3 (h) | 7.6 |
| dopamine D4.2 (h) | 30 |
| dopamine D4.4 (h) | 27 |
| dopamine D4.7 (h) | 46 |
| dopamine D5 (h) | 2000 |

Further, it was found in functional tests that the activity of (S)-2-N-propylamino-5-hydroxytetralin is purely agonistic, and a strongly pronounced functional D3 selectivity is present in comparison to the D1 receptor as well as a significant selectivity in comparison to the D2 receptor (Table 2).

TABLE 2

$EC_{50}$ value of (S)-2-N-propylamino-5-hydroxytetralin to receptor subtypes

| Receptor Subtype | $EC_{50}$ (nM) |
| --- | --- |
| D1 | 1129 |
| D2L | 2.7 |
| D3 | 0.67 |
| D4.4 | 23.4 |
| D5 | 1310 |

In comparison to (S)-2-N-propylamino-5-hydroxytetralin the structurally very similar compounds AJ76 and UH232 (Hacking & Stark, ChemBioChem 2002, 947) demonstrate a reduced D3 preference. Moreover, it was surprisingly determined that (S)-2-N-propylamino-5-hydroxytetralin has D2/D3 agonistic activity, while the structurally closely related AJ76 is described as a pure antagonist. The resulting therapeutic profile of (S)-2-N-propylamino-5-hydroxytetralin differs considerably from that of the structurally similar AJ76.

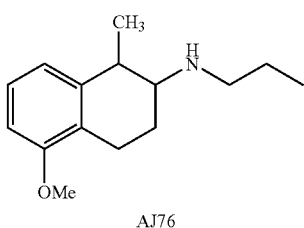

AJ76

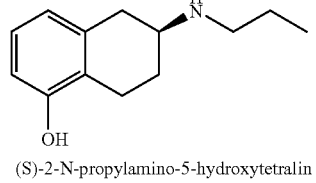

(S)-2-N-propylamino-5-hydroxytetralin

In comparison to rotigotine, from which the (S)-2-N-propylamino-5-hydroxytetralin in minimal amounts metabolically emerges, (S)-2-N-propylamino-5-hydroxytetralin shows the same agonistic effectivity ($EC_{50}$) to D3 receptor, but 564 times and 385 times less affinity to D1 and D5 receptor, respectively, and subsequently a higher selectivity for D3 in comparison to these receptors.

Consequently, an aminotetralin as high affinity D3 agonist with great functional selectivity in comparison to dopaminergic D1 and D5 receptors, considerable selectivity to D4.4 receptor and significant selectivity in comparison to D2L receptor is provided with (S)-2-N-propylamino-5-hydroxytetralin for the therapy of diseases which respond to a therapy by dopamine or dopamine agonists.

A subject matter of the present invention is thus a pharmaceutical composition comprising 2-N-propylamino-5-hydroxytetralin or its pharmaceutically acceptable salts and prodrugs thereof, wherein 2-N-propylamino-5-hydroxytetralin is preferred as a pure (S)-enantiomer.

In regard to the term "pure (S)-enantiomer" it is understood in this invention that the amount of (R)-enantiomer in the medicament is preferred with an amount of <10 mol %, more preferably with an amount of <2 mol % and most preferred with an amount of <1 mol % in regard to the total amount of 2-N-propylamino-5-hydroxytetralin in the pharmaceutical composition.

The term "pharmaceutically acceptable salts" encompasses in particular non-toxic addition salts of 2-N-propylamino-5-hydroxytetralin with organic or inorganic acids as well as their hydrates and solvates. Examples for inorganic acids comprise HCl, HBr, sulfuric acid, sulfurous acid, phosphorous acid and phosphoric acid. Organic acids comprise acetic acid, propionic acid, pyruvic acid, butyric acid, α-, β-, γ-hydroxybutyric acid, valeric acid, hydroxyvaleric acid, capronic acid, hydroxycapronic acid, caprylic acid, capric acid, lauric acid, myristic acid, palmitic acid, stearic acid, glycolic acid, lactic acid, D-glucuronic acid, L-glucuronic acid, D-galacturonic acid, glycine, benzoic acid, hydroxybenzoic acid, gallic acid, salicylic acid, vanillic acid, coumarinic acid, caffeic acid, hippuric acid, orotic acid, L-tartaric acid, D-tartaric acid, D,L-tartaric acid, meso-tartaric acid, fumaric acid, L-malic acid, D-malic acid, D,L-malic acid, oxalic acid, malonic acid, succinic acid, maleic acid, oxalic acetic acid, glutaric acid, hydroxyglutaric acid, ketoglutaric acid, adipinic acid, ketoadipinic acid, pimelic acid, glutamic acid, asparaginic acid, phthalic acid, propanetricarboxylic acid, citric acid, isocitric acid, methanesulfonic acid, toluene sulfonic acid and trifluoromethanesulfonic acid.

In this patent application the term "prodrug" of (S)-2-N-propylamino-5-hydroxytetralin describes in particular compounds understood which, in the human body, particularly in plasma or during entry through the skin or mucosa in therapeutically effective amounts, are cleaved, processed or metabolized to (S)-2-N-propylamino-5-hydroxytetralin, whereby in this patent application rotigotine as prodrug of 2-N-propylamino-5-hydroxytetralin is excluded.

As prodrugs, in particular derivatives of phenolic hydroxy groups, e.g., ester, carbonates, acetals, ketals, phosphates, phosphonates, sulfates, sulfonates, carbamates and silyl ethers come into question. Especially preferred prodrugs are esters and carbamates.

Other prodrugs can be easily enzymically cleavable, hydrolysable or unstable derivatives of the amino function of (S)-2-N-propylamino-5-hydroxytetralin, e.g., amides, carbonates or hydroxylamines. N,N-dialkyl derivatives, as e.g. the rotigotine or (S)-2-N-propylamino-5-hydroxytetralin, are on account of their stability not prodrugs in the sense of the present patent application.

The preparation of (S)-2-N-propylamino-5-hydroxytetralin can be conducted as described in the literature (see Hacksell et al., J. Med. Chem. 22, 1979, 1469; Sonesson, J. Med. Chem. 38, 1995, 1319; U.S. Pat. No. 5,442,117). The production of prodrugs via reaction of 2-N-propylamino-5-hydroxytetralin with appropriate reactive precursors like acid chlorides, acid anhydrides, carbamoyl chlorides, sulfonyl chlorides, etc. is known to the skilled person in the field of clinical chemistry. Corresponding protocols are obtainable from the relevant literature. Examples for literature citations for the production of prodrugs are Bundgaard: Design of Prodrugs, Elsevier, Amsterdam, 1985; Higuchi & Stella: Prodrugs as Novel Drug Delivery Systems, in American Chemical Society, Washington D.C., 1975; Sloan: Prodrugs—Topical and Ocular Drug Delivery, Ed: M. Dekker, 1992; Roche: Design of biopharmaceutical properties through prodrugs and analogs, Washington D.C., 1977.

The basic suitability of 2-N-propylamino-5-hydroxytetralin derivative as prodrug can for example be determined by incubating the respective compounds under defined conditions with an enzyme cocktail, a cell homogenizate or an enzyme-containing cell fraction and measuring the resulting 2-N-propylamino-5-hydroxytetralin. A suitable enzyme mix is for example included in the S 9 liver preparation of the Gentest Company, Woburn, Mass., U.S.A.

Alternatively, an incubation with fresh blood or plasma or a homogenate of the dermis can follow, in order to demonstrate a liver independent metabolism of the prodrugs as active components. For transdermal application an in vitro evaluation of permeation on excised skin is required. The final verification of the suitability and potential activity in the disease models is carried out by a measurement of the 2-N-propylamino-5-hydroxytetralin formed from the prodrug in plasma.

In vivo a prodrug should release enough (S)-2-N-propylamino-5-hydroxytetralin that a therapeutically effective steady-state concentration of (S)-2-N-propylamino-5-hydroxytetralin is achieved in plasma. In general, concentrations of (S)-2-N-propylamino-5-hydroxytetralin between 0.02 and 100 ng/ml, preferably between 0.05 and 50 ng/ml and most preferably between 0.1 and 40 ng/ml plasma are considered therapeutically effective concentrations.

A further embodiment of the invention is a pharmaceutical composition comprising a prodrug of the general formula I:

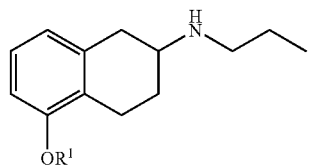

wherein $R^1$ is selected from the group consisting of alkyl, cycloalkyl, aryl, aralkyl, acyl, alkoxycarbonyl, cycloalkoxycarbonyl, aryloxycarbonyl, aralkoxycarbonyl, acetal, ketal, —C(O)NR²R³, —C(O)NHR², —S(O)₂R², —S(O)₂OR², —P(O₂H)OR², —P(O₂H)OR², wherein $R^2$ and $R^3$ are respectively selected from H, $C_{1-6}$ alkyl, $C_{3-10}$ cycloalkyl, benzyl or phenyl, and wherein a compound of formula I is present as a pure (S)-enantiomer.

Preferably $R^1$ is selected from the group of $C_{1-6}$ alkylcarbonyl, $C_{3-10}$ cycloalkylcarbonyl, benzoyl, —C(O)NR²R³ and —C(O)NHR².

"Alkyl" can be either a branched or unbranched alkyl group which preferably has 1 to 10 C-atoms, more preferably 1 to 6 C-atoms and most preferably 1, 2 or 3 C-atoms, e.g., methyl, ethyl, n-propyl, isopropyl, n-butyl, isobutyl, s-butyl, t-butyl, n-pentyl, isopentyl, neopentyl, t-pentyl, 1-methylbutyl, 2-methylbutyl, 1-ethylpropyl, 1,2-dimethylpropyl and n-hexyl. Alkyl groups can additionally be substituted with one or more substituents, for example with halogen.

"Cycloalkyl" is an alkyl group which may consist only of ring-forming C-atoms or can optionally further carry branched C-atoms. Preferred chain lengths are 3-10, more preferred 4-8 or 4-6 C-atoms.

"Alkoxy" is the group —O-alkyl, wherein alkyl is preferably selected from the above mentioned groups for "alkyl". Preferred as alkoxy is a $C_{1-6}$ alkoxy group, more preferred is a $C_{1-3}$ alkoxy group.

"Aryl" is preferably phenyl. Phenyl can be, where appropriate, additionally substituted in one or more positions, e.g., with alkoxy, alkyl, halogen or nitro.

"Aralkyl" is the group -alkyl-aryl, wherein alkyl and aryl are preferably selected from the above mentioned "alkyl" and "aryl" groups respectively. "Aralkyl" is preferably benzyl.

"Acyl" encompasses in particular the groups —C(O)-alkyl ("alkylcarbonyl"), —C(O)-cycloalkyl ("cycloalkylcarbonyl"), —C(O)-aryl ("arylcarbonyl") and —C(O)-alkyl-aryl ("aralkylcarbonyl"), wherein "alkyl", "cycloalkyl", "aryl" and "aralkyl" are preferably selected from the above-mentioned groups for "alkyl", "cycloalkyl", "aryl" and "aralkyl", whereby —C(O)—$C_{1-6}$ alkyl and —C(O)-phenyl are most preferred. Acyl is for example acetyl, propionyl, butyryl or —C(O)-phenyl ("benzoyl").

"Alkoxycarbonyl" is the group —C(O)—O-alkyl, wherein "alkyl" is preferably selected from the above-mentioned group "alkyl". Alkoxycarbonyl is preferably a $C_{1-6}$ alkoxycarbonyl group.

"Cycloalkoxycarbonyl" is the group —C(O)—O-cycloalkyl, wherein "cycloalkyl" is preferably selected from the above-mentioned "cycloalkyl" groups.

"Aryloxycarbonyl" is the group —C(O)—O-aryl, wherein "aryl" is preferably selected from the above-mentioned "aryl" groups.

"Aralkoxycarbonyl" is the group —C(O)—O-aralkyl, wherein "aralkyl" is preferably selected from the above-mentioned "aralkyl" groups.

"Ketal" is in particular the group —CR'R"—O-alkyl or —CR'R"—O-aryl bound to the phenolic oxygen atom, wherein "alkyl" and "aryl" are preferably selected from the above-mentioned groups "alkyl" and "aryl", and wherein R' and R" independently represent alkyl or aryl groups. "Acetal" differs from "ketal" in that the substituent R' in acetal is a hydrogen.

"Halogen" is preferably fluorine, chlorine, bromine or iodine.

A further embodiment of the invention is the use of 2-N-propylamino-5-hydroxytetralin, in particular as pure (S)-enantiomer, or the salts or prodrugs thereof for the preparation of a medicament for the treatment or prophylaxis of a disease selected from the group of cocaine, alcohol, opiate and nicotine addiction; neurodegenerative disorders, in particular morbus Parkinson; sexual dysfunctions, in particular male erectile dysfunction; depression, in particular endogenous monophasic depression ("major depression"); hyperprolactinemia; hyperprolactinoma; glaucoma; cognitive disorders; restless leg syndrome; attention deficit hyperactivity syndrome (ADHS); galactorrhea; acromegaly; Parkinson-associated movement disorders, e.g., rigor, dystonia and dyskinesia; L-dopa-induced disorders, idiopathic dystonia, in particular Segawa syndrome; neuroleptic-induced (tardive) dyskinesia, dystonia and akathisia, as well as Parkinson plus syndrome.

In this patent application, under the term "opiates" both naturally occurring opiates, like morphine, as well as synthetic opiates, like heroin, are subsumed.

Further, the medicaments can be used for drug-supported ablactation after pregnancy.

In particular the compounds according to the invention are suitable for the manufacture of medicament for treating L-dopa-sensitive movement disorders. Such movement disorders could be for example dyskinesia, dystonia, rigor and tremor. It is understood by the term "L-dopa-sensitive" that the movement disorder can be advantageously influenced via administration of medicaments, which influence the dopaminergic signal transduction. One typical example for this is the Segawa syndrome, an idiopathic dystonia, by which the use of L-dopa as diagnostic criteria can be used. Other examples for L-dopa-sensitive disorders are morbus Parkinson associated, or L-dopa or neuroleptic-induced movement disorders as well as the restless leg syndrome.

Morbus Parkinson associated or L-dopa or neuroleptic-induced movement disorders are for example dyskinesias, dystonias and walking disorders ("freezing"). With the use of L-dopa therapy, the so-called "wearing off" phenomenon regularly appears, which means a loss of activity of L-dopa, which can be mitigated or slowed through the use of monotherapy or combined therapy with suitable D3 dopamine agonists.

A preferred use of (S)-2-N-propylamino-5-hydroxytetralin thus relates to the manufacture of a medicament for the treatment of movement disorders, such as dyskinesias, dystonias and walking disorders, which spontaneously appear in the process of Parkinson diseases, but which may also be induced by medication. Included in the medication-induced movement disorders, like dyskinesias and dystonias, are particularly those which are induced via L-dopa or dopamine antagonists.

Finally, the pharmaceutical compositions according to the invention can also be provided, independent from the diseases to be treated, as a combination preparation for simultaneous or sequential application.

For example, a unit to be sold which comprises a medication for treatment of Parkinson's disease comprising L-dopa, can also encompass a pharmaceutical composition which comprises (S)-2-N-propylamino-5-hydroxytetralin or pharmaceutically acceptable salts and prodrugs thereof. In this case L-dopa and the compounds according to the invention can be present in the same pharmaceutical formulation, e.g., in a combination tablet, or also in different application units, e.g., in the form of two separate tablets or in two different application forms, e.g., as oral L-dopa medication and as transdermal or transmucosal (S)-2-N-propylamino-5-hydroxytetralin formulation. As according to the need, both active agents can be applied simultaneously or separately over time.

In a combination preparation, a sequential dose can be for example achieved by providing an administration form, e.g., an oral tablet, having two different layers with differing release profiles for the different pharmaceutically active components. It is clear to the skilled person that in the context of the current invention different administration forms and application schedules are possible, all of which are subject matter of the invention.

An embodiment of the invention therefore relates to a medicament which comprises L-dopa or a neuroleptic agent like (S)-2-N-propylamino-5-hydroxytetralin or a pharmaceutically acceptable salt and prodrug thereof for simultaneous or sequential application to patients.

Typically, the medicaments of the current invention consist of a pharmaceutical composition which comprises, in addition to (S)-2-N-propylamino-5-hydroxtetralin or the pharmaceutically acceptable salts and prodrugs thereof, at least one pharmaceutically acceptable carrier or adjuvant.

The pharmaceutical formulation can be differently formulated, independently of the intended manner of application. Thus the pharmaceutical formulation can for example be adjusted for intravenous, intramuscular, intracutaneous, subcutaneous, oral, buccal, sublingual, nasal, transdermal, inhalative, rectal or intraperitoneal application.

The respective formulations and the suitable pharmaceutical carriers or adjuvants for this purpose, like fillers, disintegrants, binders, lubricants, stabilizers, flavors, anti-oxidants, preservatives, dispersants or solvents, buffers or electrolytes, are known to the person skilled in the art in the field of pharmaceutics, and are for example described in standard works like Sucker, Fuchs & Speiser ("Pharmazeutische Technologie", Deutscher Apotheker Verlag, 1991) and Remington ("The Science and Practice of Pharmacy", Lippincott, Williams & Wilkins, 2000).

In one embodiment of the invention, the pharmaceutical compositions which comprise the compounds according to the invention are administered orally and can be present in the form of for example capsules, tablets, powders, granulates, coated tablets or in a liquid form.

At the same time, the formulation can be in the form of a fast release application, when a rapid onset of the effect is desired. Respective oral formulations are for example described in EP 0 548 356 or EP 1 126 821.

Suitable formulations for fast release of (S)-2-N-propylamino-5-hydroxytetralin or pharmaceutically acceptable salts and prodrugs thereof are in particular formulations for mucosal application, for example buccal or sublingual dosage forms or nasal sprays. These formulations are an ideal way to quickly counterbalance the "lows" of L-dopa-concentration which are associated with L-dopa therapy and to treat the movement disorders associated with the "off-phases" of L-dopa therapies, e.g., akinesias.

The transmucosal formulation can be in either a solid or liquid form. Solid mucosal application forms are for example quickly disintegrating sublingual tablets or mucoadhesive application forms. Preferred are liquid formulations which are suitable for use as a spray, in particular as a nasal spray.

A mucosal formulation in spray form can be in the simplest form an active ingredient solution. This can, if appropriate, be made isotonic with the addition of suitable electrolytes, e.g. sodium chloride or dextrose. A transmucosal spray of (S)-2-N-propylamino-5-hydroxytetralin or a prodrug thereof can for example be an aqueous solution, a solution in non-aqueous solvents, such as oils, glycerol or propylene glycol, or an emulsion. Further, such a transmucosal formulation can comprise buffers usual in the pharmaceutical art to adjust the desired pH of the active agent solution. Advantageously, the pH of a transmucosal formulation is set in a manner that the mucous membranes are not irritated during the application of the formulation. This is with nasal application usually the case with a mild acidic pH in the range between 3 and 6. Suitable buffers are for example acetate, citrate and phosphate buffers. Further, additional adjuvants can be present in the transmucosal formulation, e.g., in the nasal spray, as e.g., solubilizers, penetration improvers, preservatives, antioxidants, thickeners and additives for improvement of taste.

On the other hand, if a protracted release is desired, a formulation with sustained release of the active agent may be used. Respective oral and non-oral formulations are likewise known from the state of the art.

For example, (S)-2-N-propylamino-5-hydroxytetralin or the salts or prodrugs thereof may be applied in the form of patches to the skin of the patient, wherein the active agent is preferably in a matrix of adhesive polymer, e.g., a self-sticking polysiloxane adhesive. Examples for transdermal formulations are found in WO 99/49852, WO 02/89777, WO 02/89778 and WO 2004/012721. Such an administration form provides for adjusting an essentially constant plasma level and therewith a constant dopaminergic stimulation during the entire interval of application (WO 02/89778; Metman, Clinical Neuropharmacol. 24, 2001, 163).

On the other hand, if a medicament in the form of a subcutaneous or intramuscular depot form is desired, (S)-2-N-propylamino-5-hydroxytetralin, or the salts or prodrugs thereof can be suspended and injected, for example, as salt crystals, e.g. as crystalline hydrochloride, in a hydrophobic water-free medium. An example formulation is described in WO 02/15903.

Alternative pharmaceutical preparations can be for example infusion or injection solutions, oils, suppositories, aerosols, sprays, patches, microcapsules or microparticles.

EXAMPLES

Example 1

Determination of Receptor Affinities

The receptor affinities were measured using competition experiments. For this purpose the receptors are incubated with radio-labeled receptor-specific ligands. Primarily, human receptors are used which are expressed in cell lines. Alternatively, membrane preparations from rat or bovine brains are used. The incubation conditions are published and standardized. Differing concentrations of the substance ((S)-2-N-propylamino-5-hydroxytetralin) to be tested are added to the incubation preparations, in order that a dose-binding curve can be established. Unspecific binding is separated from specific binding through incubation with unspecific ligands. The proportion of specific binding in different substance concentrations is represented in % of the maximum binding of the ligand. The $IC_{50}$ value (concentration at 50% inhibition of the binding to the ligand) and the slope are determined with regression analysis. Using the Cheng-Prusoff-equation, the Ki value is determined, which then is used for comparison: the lower the Ki value, the higher the affinity (see Table 1).

Example 2

Determination of Functional Characteristics

In order to measure the intrinsic activity of the substance, human dopamine receptors were functionally expressed in cell lines (CHO-DUKX-SRE or SH-SY5Y-SRE). That means that after binding of agonists an intracellular signal cascade is activated, which leads to the formation of other proteins. The gene of one of these proteins, luciferase, was previously artificially introduced. Stimulation of the protein expression additionally leads to the formation of luciferase, which in the presence of ATP induces the emission of photons (so-called luminescence), which then can be measured photometrically. The intensity of the luminescence is proportional to the stimulation of the receptors. Dopamine agonists stimulate the luminescence while antagonists do not lead to a specific effect. However, antagonists inhibit the luminescence induced via either dopamine or agonist. The activity in different substance concentrations is represented in % of maximal activity via the endogenous ligand or a suitable agonist. The $EC_{50}$ value (concentration at 50% activation) and the slope are determined using regression analysis. Using the Cheng-Prusoff-equation, the Ki value is determined, which then is used for comparison: the lower the Ki value, the higher the affinity and activity. In regard to the effect of (S)-2-N-propylamino-5-hydroxytetralin on dopamine receptors, the values provided in Table 2 were found.

Example 3

In Vitro Reaction of a Prodrug into the Active Substance

From liver cell homogenates from human, primate, dog, rat or mouse, the microsome fraction which comprises the primary metabolic enzymes recovered by differential centrifugation; alternatively, the cytoplasmic fraction can also be recovered. The subcellular fraction is suspended with a buffer to obtain a solution with a defined amount of protein. After addition of 1 µM of the prodrug to be tested, an incubation follows at 37° C. for 60 min. Subsequently, (S)-2-N-propylamino-5-hydroxytetralin is quantified using HPLC/UV or using HPLC/MS and put into relation with the used amounts. For detailed analysis, concentration curves or time courses are investigated.

Example 4

Depot Suspension (a) 1411.2 g Miglyol 812 is weighed out into a Duran flask. 14.4 g Imwitor 312 was added to the Miglyol and subsequently was heated for 30 minutes to 80° C. while stirring. The clear solution was cooled to room temperature and filtered.

(b) 1188 g of the solution produced in (a) was transferred to a glass laboratory reactor, 12 g of active agent was added and homogenized for 10 minutes with an Ultraturrax at 10,000 rpm under nitrogen. The suspension was filled with running Ultraturrax (2,000 rpm) in brown glass flasks.

The invention claimed is:

1. A pharmaceutical composition comprising (S)-2-N-propylamino-5-hydroxytetralin or a pharmaceutically acceptable salt or prodrug thereof, and at least one pharmaceutically acceptable carrier or adjuvant, wherein the prodrug is of the formula

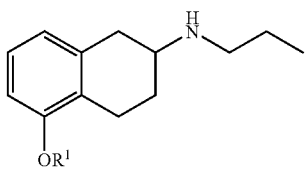

or a salt thereof;
wherein $R^1$ is selected from the group consisting of acyl, alkoxycarbonyl, cycloalkoxycarbonyl, aryloxycarbonyl, acetal, ketal, —C(O)NR²R³, —C(O)NHR², —P(O₂H)OR² and —P(O₂H)R², wherein $R^2$ and $R^3$ are independently selected from H, $C_{1-6}$ alkyl, $C_{3-10}$ cycloalkyl, benzyl and phenyl and wherein the at least one pharmaceutically acceptable carrier or adjuvant is selected from the group consisting of fillers, disintegrants, binders, lubricants, stabilizers, flavors, antioxidants, preservatives, dispersants, buffers and electrolytes; and wherein the pharmaceutical composition is in a form selected from the group consisting of an infusion solution, an injection solution, an oil, a suppository, a patch, a microcapsule and a microparticle.

2. The composition of claim 1, comprising (S)-2-N-propylamino-5-hydroxytetralin or a pharmaceutically acceptable salt thereof.

3. The composition of claim 1, comprising a prodrug or a salt thereof wherein $R^1$ is selected from $C_{1-6}$ alkylcarbonyl, $C_{3-10}$ cycloalkylcarbonyl, benzoyl, —C(O)NR²R³ and —C(O)NHR².

4. The composition of claim 1, wherein the (S)-2-N-propylamino-5-hydroxytetralin or salt or prodrug thereof is present as a pure (S)-enantiomer.

5. A compound having the formula

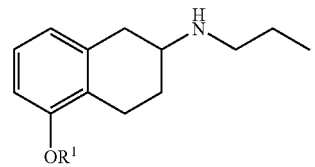

or a salt thereof;
wherein $R^1$ is selected from the group consisting of acyl, alkoxycarbonyl, cycloalkoxycarbonyl, aryloxycarbonyl, acetal, ketal, —C(O)NR²R³, —C(O)NHR², —P(O₂H)OR² and —P(O₂H)R², wherein $R^2$ and $R^3$ are independently selected from H, $C_{1-6}$ alkyl, $C_{3-10}$ cycloalkyl, benzyl and phenyl;

said compound being in the (S)-configuration; and wherein said compound, when administered to a human body, is cleaved, processed or metabolized to (S)-2-N-propylamino-5-hydroxytetralin.

6. The compound of claim 5, wherein $R^1$ is selected from $C_{1-6}$ alkylcarbonyl, $C_{3-10}$ cycloalkylcarbonyl, benzoyl, —C(O)NR²R³ and —C(O)NHR².

* * * * *